United States Patent
Edwards et al.

(10) Patent No.: US 7,330,579 B2
(45) Date of Patent: Feb. 12, 2008

(54) AUTOMATED INSPECTION OF TINTED OPHTHALMIC PARTS

(75) Inventors: Russell J. Edwards, Jacksonville, FL (US); Gary S. Hall, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 705 days.

(21) Appl. No.: 10/706,561

(22) Filed: Nov. 12, 2003

(65) Prior Publication Data

US 2004/0114135 A1    Jun. 17, 2004

Related U.S. Application Data

(60) Provisional application No. 60/425,938, filed on Nov. 13, 2002.

(51) Int. Cl.
*G06K 9/00* (2006.01)

(52) U.S. Cl. .................................. 382/141; 382/143

(58) Field of Classification Search ............... 382/141, 382/143, 152; 348/86, 92, 125, 128, 129
See application file for complete search history.

(56) References Cited

U.S. PATENT DOCUMENTS

| | | | |
|---|---|---|---|
| 4,634,449 A | 1/1987 | Jenkins | |
| 4,668,240 A | 5/1987 | Loshaek | |
| 4,705,370 A | 11/1987 | Johnson | |
| 4,733,959 A | 3/1988 | Claussen | |
| 4,777,684 A | 10/1988 | Johnson | |
| 4,872,404 A | 10/1989 | Quetsch | |
| 4,889,421 A | 12/1989 | Cohen | |
| 4,898,695 A | 2/1990 | Doshi | |
| 4,946,269 A | 8/1990 | Magdassi | |
| 4,963,159 A | 10/1990 | Narducy | |
| 4,981,487 A | 1/1991 | da Costa | |
| 4,997,897 A | 3/1991 | Melpolder | |
| 5,034,166 A | 7/1991 | Rawlings | |
| 5,055,602 A | 10/1991 | Melpolder | |
| 5,094,609 A | 3/1992 | Kindt Larsen | |
| 5,116,112 A | 5/1992 | Rawlings | |
| 5,120,121 A | 6/1992 | Rawlings | |
| 5,151,106 A | 9/1992 | Bhaumik | |
| 5,160,463 A | 11/1992 | Evans | |
| 5,244,470 A | 9/1993 | Onda | |
| 5,255,077 A | 10/1993 | Yamazaki | |
| 5,271,874 A | 12/1993 | Osipo | |
| 5,271,875 A | 12/1993 | Appleton | |
| 5,292,350 A | 3/1994 | Molock | |
| 5,377,002 A | 12/1994 | Nesensohn et al. | |
| 5,443,152 A | 8/1995 | Davis | |

(Continued)

FOREIGN PATENT DOCUMENTS

EP    0 686 842    12/1995

(Continued)

OTHER PUBLICATIONS

PCT International Search Report, dated May 27, 2004, for PCT Int'l. Appln. No. PCT/US03/36378.

(Continued)

*Primary Examiner*—Vikkram Bali

(57) ABSTRACT

Methods, systems and apparatuses for inspecting tinted ophthalmic parts are disclosed.

16 Claims, 10 Drawing Sheets

U.S. PATENT DOCUMENTS

| | | |
|---|---|---|
| 5,452,658 A | 9/1995 | Shell |
| 5,466,147 A | 11/1995 | Appleton |
| 5,500,732 A | 3/1996 | Ebel |
| 5,528,357 A | 6/1996 | Davis |
| 5,534,038 A | 7/1996 | Evans |
| 5,568,715 A | 10/1996 | Ebel |
| 5,578,331 A | 11/1996 | Martin |
| 5,640,464 A | 6/1997 | Ebel |
| 5,649,410 A | 7/1997 | Martin |
| 5,675,962 A | 10/1997 | Martin |
| 5,687,541 A | 11/1997 | Martin |
| 5,745,230 A | 4/1998 | Edwards |
| 5,748,300 A | 5/1998 | Wilder |
| 5,792,822 A | 8/1998 | Miyabayashi |
| 5,805,276 A | 9/1998 | Davis |
| 5,812,254 A | 9/1998 | Ebel |
| 5,824,276 A | 10/1998 | Janssen |
| 5,824,719 A | 10/1998 | Kunzler |
| 5,828,446 A | 10/1998 | Davis |
| 5,846,457 A | 12/1998 | Hoffman |
| 5,871,675 A | 2/1999 | Muller |
| 5,938,795 A | 8/1999 | Molock |
| 5,943,436 A | 8/1999 | Ebel |
| 5,995,213 A | 11/1999 | Davis |
| 6,007,229 A | 12/1999 | Parnell, Sr. |
| 6,047,082 A * | 4/2000 | Rhody et al. ............... 382/141 |
| 6,048,371 A | 4/2000 | Tipton |
| 6,096,799 A | 8/2000 | Benz |
| 6,132,043 A | 10/2000 | Atkins |
| 6,149,842 A | 11/2000 | Lally |
| 6,154,274 A | 11/2000 | Davis |
| 6,196,683 B1 | 3/2001 | Quinn |
| 6,246,062 B1 | 6/2001 | Ross, III |
| 6,248,266 B1 | 6/2001 | Gartley |
| 6,322,214 B1 | 11/2001 | Atkins |
| 6,348,507 B1 | 2/2002 | Heiler |
| 6,364,934 B1 | 4/2002 | Nandu |
| 6,368,572 B1 | 4/2002 | Reisner |
| 6,577,387 B2 * | 6/2003 | Ross et al. .................. 356/124 |
| 2002/0080327 A1 | 6/2002 | Clark |
| 2002/0133869 A1 | 9/2002 | Molock |
| 2003/0227596 A1 | 12/2003 | Clark |

FOREIGN PATENT DOCUMENTS

| | | |
|---|---|---|
| EP | 1 016 860 | 7/2000 |
| WO | WO 02/057837 A2 | 7/2002 |

OTHER PUBLICATIONS

U.S. Appl. No. 10/027,579, Johnson & Johnson Vision Care, Inc.

* cited by examiner

AUTOMATED INSPECTION OF TINTED OPHTHALMIC PARTS

RELATED APPLICATIONS

This application is a non-provisional filing of a provisional application U.S. App. No. 60/425,938, filed on Nov. 13, 2002.

FIELD OF THE INVENTION

This invention relates to the inspection of cosmetically tinted contact lenses or molds that are used in the formation of the tinted contact lenses, more particularly to pad printed molds that are used in the formation of the tinted contact lenses.

BACKGROUND OF THE INVENTION

The inspection of untinted contact lenses is known. Techniques and systems for inspecting untinted contact lenses are disclosed in U.S. Pat. Nos. 6,246,062; 6,154,274; 5,995,213; 5,943,436; 5,828,446; 5,812,254; 5,805,276; 5,748,300; 5,745,230; 5,687,541; 5,675,962; 5,649,410; 5,640,464; 5,578,331; 5,568,715; 5,443,152; 5,528,357; 5,500,732; 4,981,487; 5,244,470; 6,196,683; 4,668,240; 5,824,719; 4,963,159; 4,946,269; 4,872,404; 4,898,695; 5,255,077; 4,634,449; 4,705,370; 4,777,684; 4,733,959; 5,271,874; 4,889,421; 5,055,602; 5,034,166; 4,997,897; 5,116,112; 5,120,121; 5,871,675; 5,938,795; 6,048,371; 6,132,043; 6,322,214; 6,364,934; 6,149,842; 6,096,799; 5,846,457; 5,824,276; 5,792,822; 5,534,038; 5,452,658; 5,292,350; 5,160,463; 6,248,266; 5,151,106; 5,271,874; 5,271,875; 5,466,147; and 6,348,507, all of which are hereby incorporated by reference in their entireties. Additionally methods of tinting contact lenses have been disclosed in the following applications, U.S. patent application Ser. No. 09/745,511 filed Dec. 22, 2000; U.S. patent application Ser. No. 09/792,671 filed Feb. 23, 2001; U.S. patent application Ser. No. 10/027,579 filed Dec. 20, 2001; U.S. patent application Ser. No. 10/165,058 filed Jun. 7, 2002 all of which are hereby incorporated by reference in their entireties.

Before this invention, automated inspection techniques had not been used for inspecting the application of tint to a tinted contact lens. The application of the tint was either not inspected or it was done manually, by operators who visually inspect each lens to determine if the tint contains any irregularities, and if the layers of tint are concentric to the edge of the mold. If any irregularity or flaw in the tint was found and it made the lens unsuitable for consumer use, the lens was identified so that it was not subsequently sold to a consumer.

This prior art inspection system is subject to human error. Additionally, a manual inspection step would likely be located after the lens has gone through most, if not all, of the manufacturing steps. An automated inspection system that could be inserted at any convenient location within the manufacturing line would be desirable to avoid fully processing lenses that will ultimately be rejected. Additionally, if the inspection system is immediately after the application of the colorant to a lens or to a lens mold, then if there are a high number of rejects, a problem within the area of the machine where the colorants are applied can be immediately addressed, and not discovered much later during production after many more lenses have been made having a defect in the colorant.

This invention provides a method and system that inspects the tint and/or printed patterns on a contact lens or mold for molding a contact lens therein. The method and system finds defects including voids in the colorant, excess colorant, and incorrect position of the colorant and/or pattern(s) of the colorant with respect to the center and/or edges of the ophthalmic products, e.g. mold or contact lens or other colorant layers.

One benefit of this invention is that the inspection does not have to be done on finished lenses, but can be done immediately after the colorant is added to the mold or lens. This provides immediate feedback to the machine to reject for various defects and allows the machine operator to react quickly if numerous defects in the colorant are being made. An additional benefit is that because defects are difficult to define, standardize and learn, human inspection often gave inconsistent results, whereas the automated system gives more consistent results. This invention also comprises the system described herein for performing the method of this invention.

DETAILED DESCRIPTION OF THE INVENTION

This invention provides a method for inspecting ophthalmic parts comprising colorants the method comprising, consisting essentially of, or consisting of the steps of:

a) capturing an image of said ophthalmic part comprising at least one colorant wherein said image comprises an array of pixels and said at least one colorant is present in a portion of said image;

b) locating a reference means in said image of said ophthalmic part and finding the center of said reference means;

c) locating at least one first pixel area in the portion of said image of said ophthalmic part comprising said at least one colorant;

d) comparing the location of said at least one first pixel area to the location of a first pixel standard to determine the location of said colorant center, and comparing the location of the center of said reference means to the location of said colorant center to determine if said at least one colorant is properly located on said ophthalmic part.

As used herein, the term "ophthalmic part" refers to a tinted contact lenses or transparent or semi-transparent object used in the production of the tinted contact lenses. Ophthalmic parts may be tinted by a number of methods which include but are not limited to pad printing on the contact lens, pad printing on the lens mold, tinting in a solution, adding colorants to the reaction mixture used to form the contact lens; however, the preferred ophthalmic parts are lens molds that are pad printed with colorants. As used herein, the term "colorant" means any organic or inorganic composition that may be used to impart a visible color an article. The inspection of a pad printed lens mold having colorant thereon will be described below, but these methods may be applied to all tinted ophthalmic parts.

When lens molds are tinted, the colorant can be applied in single or multiple layers of transparent colorants and/or opaque colorants or combinations of any of those. The methods and system of the invention inspect and verify the print quality and registration tolerance (either or both concentricity and the pattern to pattern distance) of each printed layer of colorant either step-wise after each individual colorant layer is applied or in one step after all the colorant has been applied to the lens mold. If multiple colorant layers are applied the colorants are typically applied in individual layers that typically overlap, although colorant layers that do not overlap could be inspected using the machine vision system described herein. Additionally, there may be a clear binder layer added to the ophthalmic part as a separate layer without added colorant, which may be referred to as a "foundation layer". This layer is typically transparent so unless there is a major defect in the binder layer, it will not be inspected in the method of this invention.

Figure 1:
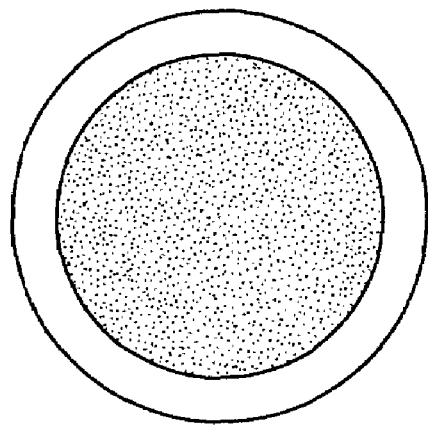
FIG. 1 is a transparent layer on an ophthalmic part.
Figure 2:
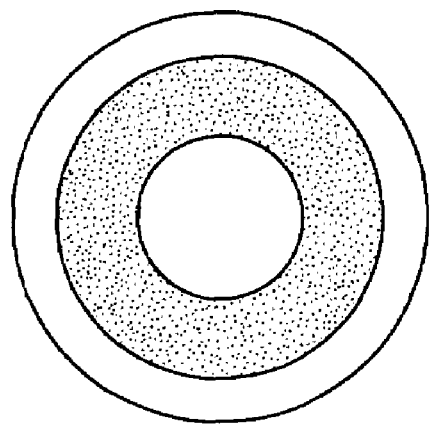
FIG. 2 is a transparent layer on an ophthalmic part.
Figure 3:
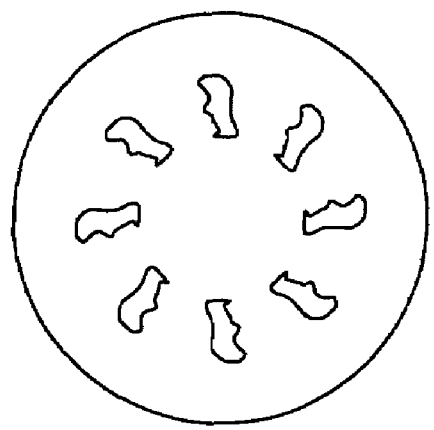
FIG. 3 is a colorant striae layer on an ophthalmic part.
Figure 4:
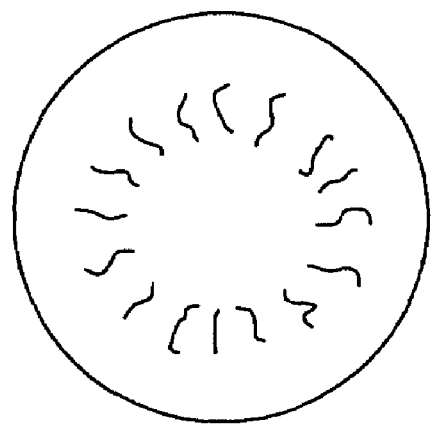
FIG. 4 is a colorant feather layer on an ophthalmic part.

Currently, there are two types of tinted contact lenses in the industry. Enhancer contact lenses enhance a user's natural iris color and opaque contact lenses change the user's natural iris color. Both types of lenses can be made by using lens molds containing colorant. The enhancer contact lens mold is composed of at least one layer of translucent colorant. The translucent colorant is applied in one or more layers to a circular area of the contact lens covering the iris and pupil area or to a donut-shaped (iris-shaped) area of the contact lens covering only the iris of the contact lens wearer. The transparent layers of the enhancers are shown in FIGS. 1 (covering the iris) and 2 (iris-shaped). Opaque contact lens molds contain 2 or more layers of opaque and/or translucent layers in any combination. Preferably the opaque contact lens molds contain at least one translucent layer as shown in FIG. 1 or 2, and at least one opaque layer. The opaque layers typically are not solid colorant layers that cover the entire iris, but consist of patterns within a boundary having a donut-shape (iris shape), such as shown in FIGS. 3 and 4. FIGS. 3 and 4 show the patterns that make up a striae layer and a feather layer, respectively; however, any pattern e.g. consisting of dots, or cross-hatches, etc. can be used to create the colorant patterned layers of the opaque lens. In one preferred embodiment, the contact lens molds comprise a binder layer, a translucent layer, an opaque layer comprising a striae design and may be referred to as the "striae layer" and another opaque layer comprising a feather design and may be referred to as the "feather layer". However, the inspection methods and system described herein can be used to inspect enhancers, and opaque contact lens molds with any number or combination of layers.

In the preferred embodiment, the tinted mold, is preferably the front curve lens mold which may or may not be attached to a frame, mounted onto a pallet are pad printed with layers of colorant as described in U.S. patent application Ser. Nos. 09/745,511; 09/792,671; 10/027,579; and 10/165,058, incorporated earlier by reference. After printing, the molds are conveyed to the inspection system. Molds, frames and pallets have been disclosed in the prior art, such as, U.S. Pat. Nos. 5,094,609; 6,368,572 and 6,007,229, incorporated herein in their entireties.

Figure 8:
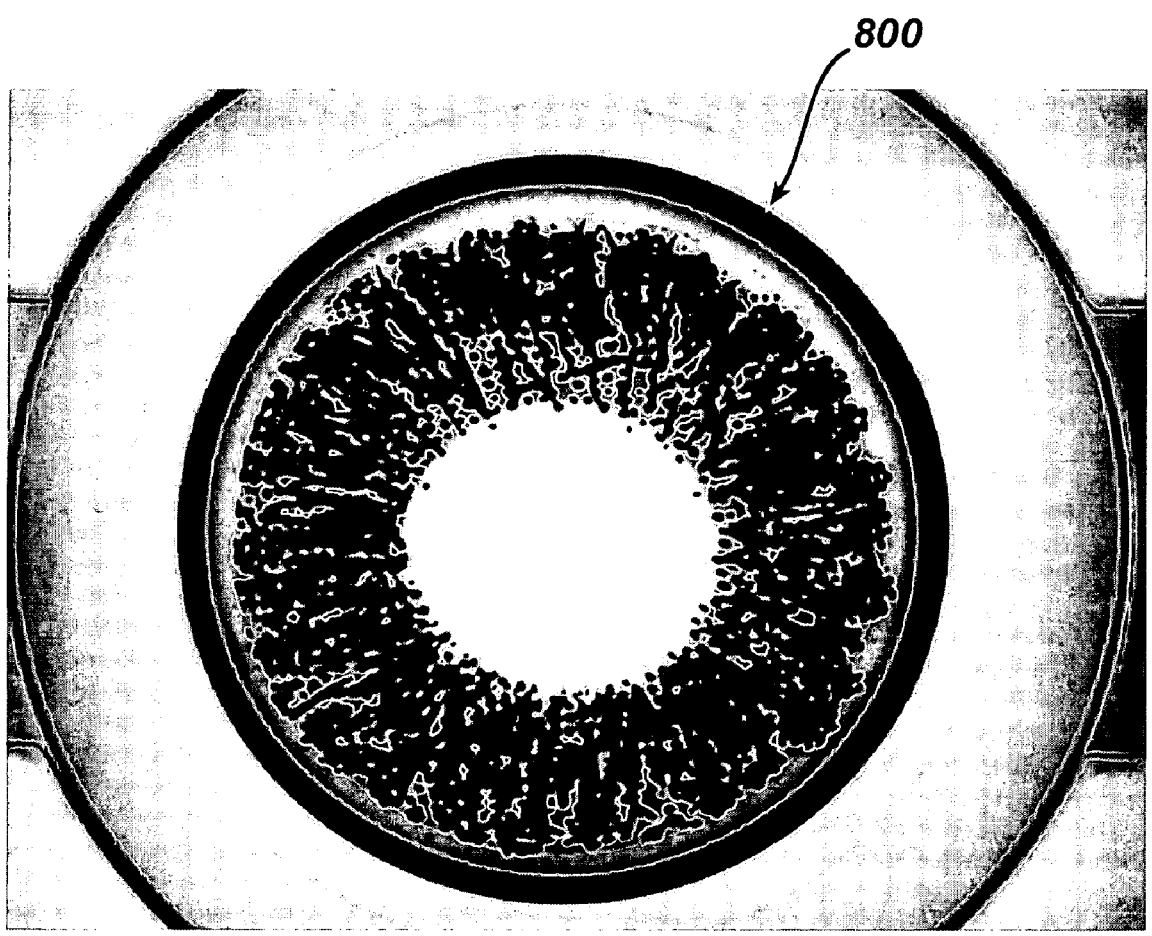
FIG. 8 is a scan of a single image captured by the system shown in FIG. 5.

As used herein, the term "reference means" defines an area of the captured image that does not contain a colorant. The reference means may be the knife edge, outside edge of the mold, tab, or a feature added to the lens mold, such as a hatch mark, or the like, added to the mold specifically to be a registration means. In the preferred embodiment, the reference means is the knife edge 800 which as shown in FIG. 8 shows up as a dark circular line; that is, a circular pattern of low intensity pixels (on a gray scale of 0-255, low intensity is less than or equal to about 30) in the pixel image. Alternatively, for a contact lens, the reference means could be the lens edge, which can be located as described in U.S. Pat. No. 5,500,732. The same gradient process described in U.S. Pat. No. 5,500,732 or in U.S. Pat. No. 5,640,464 that is used to locate the edges of a package can be modified by a person of ordinary skill in the art and used herein to locate the knife edge or outside edge of the mold.

Figure 9:
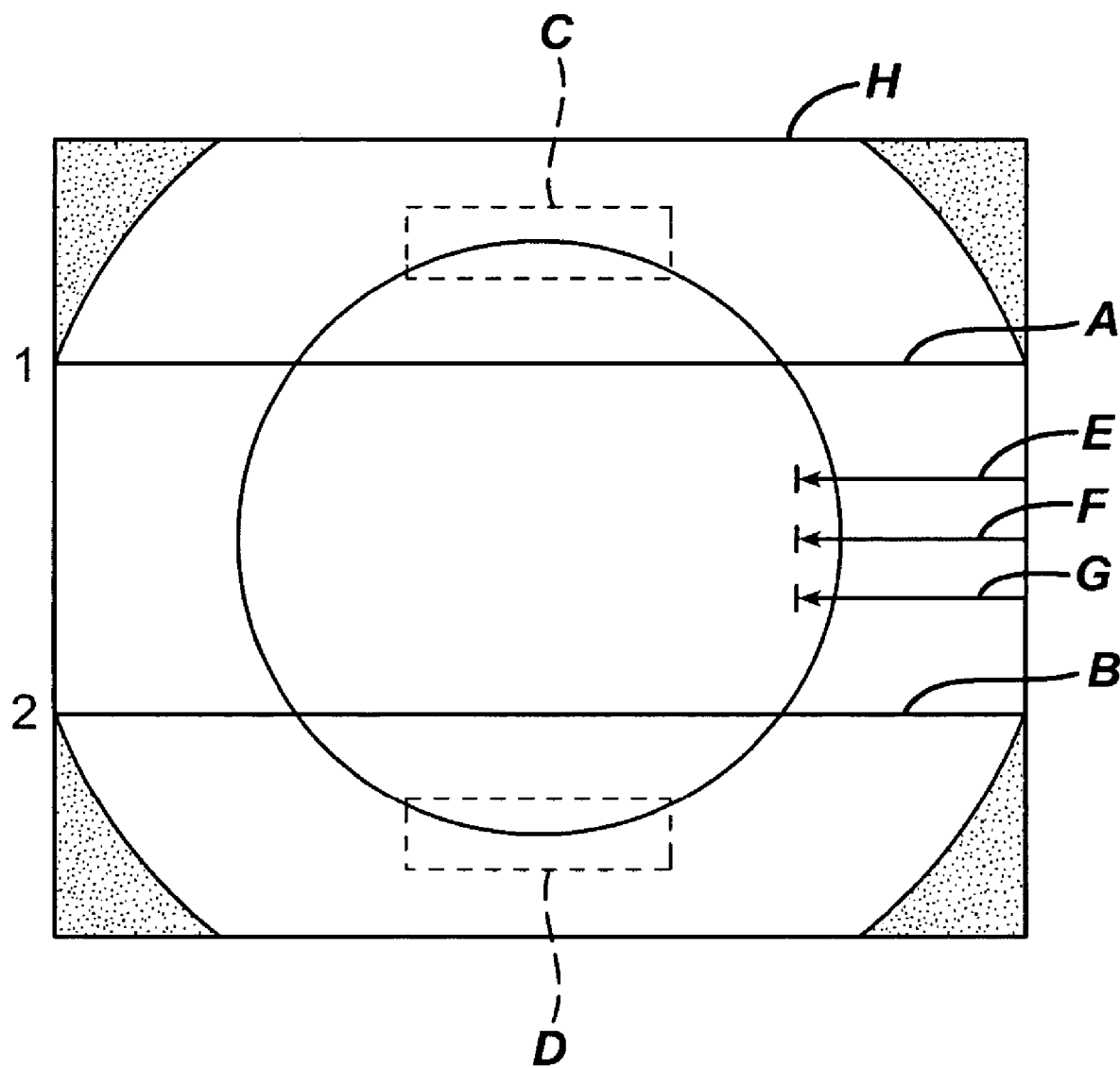
FIG. 9 illustrates schematically two search vectors across the image captured by the system shown in FIG. 5.

Alternatively, the knife edge can be found by performing a gradient process starting from the boundaries of the captured image and searching one or more vectors (E, F, G shown in FIG. 9), of pixels that only go a short distance from the boundary of the captured image (perimeter H, of FIG. 9) into the pixel image, or by searching only small areas of pixels for example in areas marked C and D shown in FIG. 9, because given the set geometry of the system the location of the knife edge will be approximately the same from image-to-image. Finding the knife edge in either of those ways will limit the number of pixels that need to be analyzed to find the low intensity circular line that is the knife edge. These techniques are described in U.S. Pat. No. 5,500,732. Once the knife edge has been located, the algorithm preferably calculates the center of the reference means, that is the center of the mold.

As used herein, the phrase "first pixel area" refers to an area of the lens mold image containing colorant. This area must be distinguishable from other areas containing colorant. Preferably, the first pixel area covers an area on the lens mold image of about 5×5 pixels, but can be larger. This first pixel area may be anywhere in the image other than the Optical Zone (defined hereinafter) or the reference means (defined hereinafter). Preferably, the first pixel area is in the area of the image equivalent to the iris of an eye. As used herein, the phrase "second pixel area" refers an area of the lens mold image having the same characteristics as the first pixel area, but located in a different portion of the image. An additional calculation of the center of the colorant may be determined by using the second pixel area. This center, when averaged with the center from the first colorant, will add to the accuracy of the center calculation. Increased accuracy may be necessary to accommodate the variation and distortion of the printed pattern. Further accuracy may be gained by similarly calculating centers from additional pixel areas.

Models of the colorant designs that are printed on the ophthalmic parts can be made by a number of methods. Pictures of said designs can be obtained or commercially developed graphics design packages may be used to replicate these designs. In the circumstances when the design consists of many layers, a model of each layer may be prepared. In this invention, it is preferred that computer generated models of the colorant designs are used. As used herein, the phrase, "first pixel standard" refers to an area in a model of the colorant design. This area must be distinguishable from other areas containing colorant. Preferably, the first pixel standard covers an area of the model of about 5×5 pixels, but can be larger. This first pixel standard may be anywhere in the model other than the equivalent of the Optical Zone (defined hereinafter) or the reference means (defined hereinafter). Preferably, the first pixel standard is in the area of the image equivalent to the iris of an eye. As used herein, the phrase "second pixel standard" refers an area of the model having the same characteristics as the first pixel standard, but located in a different portion of the model.

As used herein, "capturing an image" can be accomplished as described in U.S. Pat. No. 5,500,732. In the presently preferred mode, the lighting is done with a constant-on (LED-Light Emitting Diode), white light source, using an electronic shutter mechanism on the camera to capture the image when the molds are properly positioned and stationary under the cameras. If manufacturing requirements increase and fast conveying of the molds becomes necessary the imaging step could be accomplished using a strobe with moving parts as described in U.S. Pat. No. 5,500,732. The frames or pallets carrying the molds are conveyed under the cameras, and above the lighting source, the shutter of the cameras is activated and the cameras capture an image of the mold carrying the colorant. The cameras may be gray-scale or color cameras. If a color camera is used the image will be divided into the red, green and blue layers on 3 chips in the color camera. If the camera is a gray-scale image the intensity of the light in the image is assigned a value of 0 to 255 for each pixel in the image. Preferably, a 1024 by 1024 pixel array is used to capture the image for the single gray-scale image, although less or more resolution can be used if desired. For the color arrays, preferably fewer pixels are used, e.g., 768 by 494 pixel arrays for each color image, because more calculations have to be performed when three colors are captured within an individual images. FIG. 8 shows a single image of a mold and all the colorant layers thereon. It is presently preferred to capture a color image of the mold and the colorant layers, so that the captured image can be separated into the red, green and blue portions of the entire image.

Figure 5:
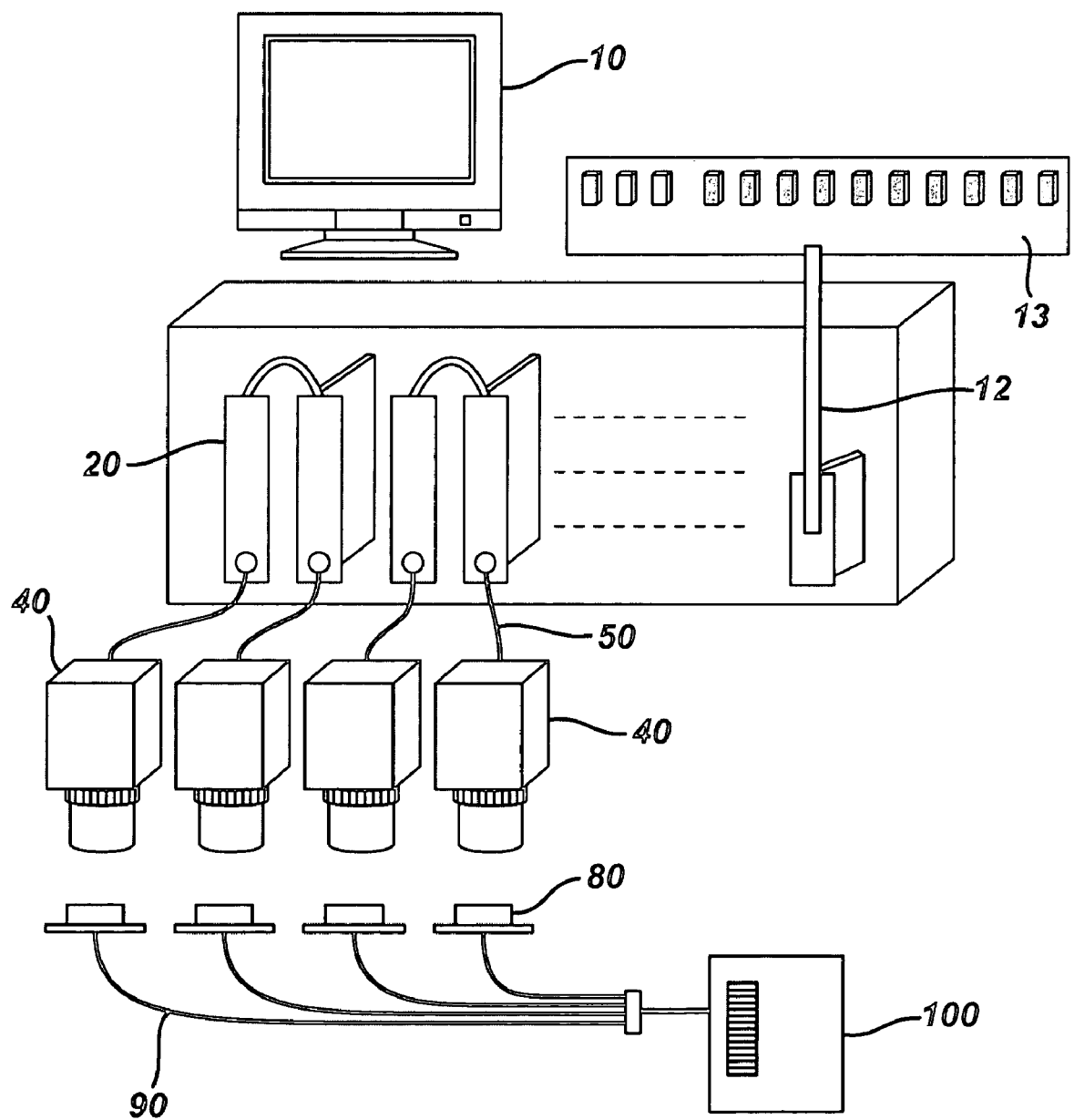
FIG. 5 is a system of the invention.

The preferred system is shown in FIG. 5. FIG. 5 shows four cameras 40. The cameras are preferably color cameras, Sony XC-003 having having a 55 mm focal length Telecentric lenses 70 (with 0.75× Extension) with a 5 mm spacer between the camera body and the telecentric lens. The cameras are focused above a surface (not shown) upon which the lens curve molds (not shown) optionally on pallets (not shown) are pushed, so that the cameras are focused onto the lens curves (not shown). In the surface (not shown) are holes through which light from light sources 80 is directed at the lens curves. The light sources are attached to a power supply 100 via power cables 90.

Any conveyor mechanism can be used, for example a pusher arm or walking beam as described in U.S. Pat. No. 5,500,732, which is hereby incorporated by reference in its entirety. The molds attached to the frame can be conveyed without a pallet, individual molds are preferably conveyed on a pallet. The frame or pallet may ride on the surface in a channel directed by guide rails. Four lens curves (not shown) are placed between the cameras 40 and the light sources 80. Alternatively, the cameras may be mounted underneath the surface on which the pallets are conveyed facing up to allow imaging of the convex side of the pattern. An image of the colorant on the mold is captured by camera 40 and communicated via cables 50 to the Vision Processor/Frame Grabber 20 for processing. The Processor/Frame Grabber 20 is housed within computer 10.

The software in the PC contains various algorithms that analyze the image of the lens mold having the colorant thereon. The decision is sent via the PB 24 Opto IO Rack 13 and cable 12 to an external PLC computer (not shown) that controls a material handling device. This device will either allow the mold having colorant layer(s) thereon to continue through the process of manufacturing the tinted contact lens or it will remove it from further material processing.

The next step is to analyze the captured image or images to determine if the colorant is properly oriented on the ophthalmic part. The reference means of the image and the center of the reference means are located as previously discussed. As shown in FIG. 9 the intensity values of the pixel image are scanned in multiple lines either across or up and down the image (lines A, B across two rows of pixels are shown) to find a reference means. After scanning the image, and locating adjacent pixels having low intensity that are part of the knife edge, the algorithm can define the circular knife edge by calculating the circumference of the circle. Additional points can be located either before or after the circle is calculated to check for a misshapen mold, or to verify that the knife edge has been properly located.

If a single gray scale image of the colorant layer(s) is processed to determine the position of the design in the lens mold, then all three colorant layers may be treated as a single shape and the same gradient techniques described above that were used to locate the knife edge or outside edge of the mold in the pixel image are used to find the inside and/or outside boundaries of the single colorant layer shape. Using the location of the first pixel area and the location of the first pixel standard, the center of the colorant may be found. If location of the calculated colorant center is not within a specific distance of the location of the center of the reference means, ophthalmic part is rejected. Preferably parts are rejected if the distance between the center of the reference means and the colorant center are greater than about 0.9 mm, more preferably greater than about 0.6 mm, preferably greater than about 0.550 mm, more preferably, greater than about 0.300 mm, most preferably greater than about 0.200 mm.

For the preferred embodiment three color images (red, green and blue color images) are created by the camera. The reference means on the ophthalmic part is found on at least one of the color images using the gradient technique described above, and then the algorithm calculates the location of the center of reference means. Each color pixel image is analyzed using any the gradient processes, previously described, to locate the first pixel area and the colorant center of the colorant layers. If parts of the individual layers are occluded by others, the visible parts of the layers are identified. Alternatively, when the design has multiple layers, the individual layers are compared to a previously stored pattern that was created by a commercially available graphics design package. The colorant centers of each individual layer may be calculated as described above. Then, either the individual colorant centers determined from the individual color images are compared to each other or to the reference center to determine if the colorant layer or layers are in the proper location. If the centers are not within a specified distance from each other, preferably no than about 0.9 mm, more preferably greater than about 0.6 mm, preferably greater than about 0.550 mm, more preferably, greater than about 0.300 mm, most preferably greater than about 0.200 mm, the ophthalmic part is rejected.

If using the outer edges of the pattern in the one or more colorant layers to form a circle to determine the center of the colorant layer is problematic since the outer edges of the pattern in the colorant layer may vary in their distance from the center of the colorant layer, the algorithm can be modified to search along a circle made midway through the expected location of the colorant layer. Along this circle, known features of the pattern are identified. Further, when several features of the pattern are identified, the center of the pattern is known, because the expected pattern is known.

A further aspect of the invention provides a method for inspecting ophthalmic parts comprising colorants the method comprising, consisting essentially of, or consisting of the steps of:
 a) capturing an image of said ophthalmic part comprising at least one colorant wherein said image comprises an array of pixels and said at least one colorant is present in a portion of said image;
 b) locating a reference means in said image of said ophthalmic part and finding the center of said reference means;
 c) analyzing said portion of said image comprising at least one colorant to determine the dimension of said portion and finding the colorant center of said image;
 d) comparing the location of the center of said reference means to said colorant center to determine if said at least one colorant is properly located on said ophthalmic part.

The terms ophthalmic part, colorant, reference means, colorant center, and capturing an image all have their aforementioned meanings and preferred ranges. The terms "analyzing said portion" refers to measuring the contrast (difference in intensity) between the colorant portion and the remainder of the lens mold and using those measurements to calculate the circular area of that portion and its colorant center, using known non-linear regression analysis or known area-weighted (centroidial) calculations. Once the location of the colorant center is known, it may be compared with the location of the reference center as previously described to determine if the lens mold may be used to prepare a tinted contact lens.

Another aspect of the present invention is a method for inspecting ophthalmic parts comprising colorants the method comprising, consisting essentially of, or consisting of the steps of:
 a) capturing an image of said ophthalmic part having at least one colorant wherein said image comprises an array of pixels and said at least one colorant is present in a portion of said image;
 b) capturing a reference image of a standard ophthalmic part wherein said reference image comprises an array of pixels and said at least one colorant is present in a portion of said reference image;
 c) comparing the intensities of the image from step a) with the reference image from step b) to determine whether the image from step a) contains defects.

The terms ophthalmic part, colorant, and capturing an image all have their aforementioned meanings and preferred ranges.

The terms "reference image" and "standard ophthalmic part" refers to an image of an acceptable ophthalmic part which be used as the standard for judging other ophthalmic parts. The term "defects" refers to either the absence of colorant in a particular area of an ophthalmic part, (a void) or the presence of too much colorant (an excess) in a particular area of an ophthalmic part. The preferred ranges for defects shall be described in detail in later paragraphs.

In the preferred embodiment, reference images are captured by a camera 40 and taught to the Vision Processor/Frame Grabber 20 for processing in computer 10 (FIG. 5) and stored in that system. Preferably the system is taught by imaging an ophthalmic part with an acceptable colorant layer thereon and having the system generate a pixel map for each of the color images in that colorant layer. If the ophthalmic part has multiple color layers, this step is repeated for all colorant layers to be applied to the ophthalmic part, and for the ophthalmic part having all the colorant layers. The system generates individual images (pixel maps) for each individual colorant layer and for the all the colorant layers together. These images (pixel maps) can be used while performing inspections to analyze the images of the ophthalmic parts to be inspected. Alternatively, an ophthalmic part having all colorant layers can be taught to the system in a single step, and the system can develop the individual pixel maps by extracting the individual colorant layers from the full image.

The intensities of the image of the part to be inspected and the reference image can be compared as a whole, by analyzing all portions of each image in a systematic matter. In the preferred embodiment, the images may be compared in discrete zones.

Figure 10:
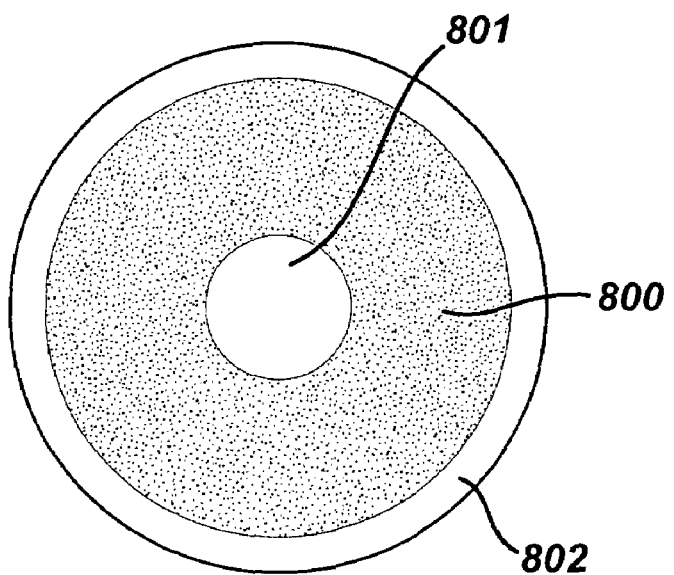
FIG. 10 illustrates the search zones in the ophthalmic part.

As shown in FIG. 10, the zones include the optical zone 801, the iris pattern zone 800 and the knife edge zone 802. By defining the zones, the algorithm can begin its analysis of the pixels within each zone.

The optical zone and the knife edge zone are checked to be sure that there is no stray colorant in those areas. Colorant can mistakenly drip, or splash in the optical zone or knife edge zone by the pad printing equipment, or be present within these zones by the application of a improperly located colorant layer. In the preferred embodiment the optical zone is the central 4 mm of the image. For this analysis, values for the sensitivity threshold, which is an allowable contrast in intensity between neighboring pixels, minimum defect size, which is an area in which the intensity values of the pixels are not within an acceptable range of intensities, and the defect size thresholds, which is the minimum allowable sum of the area of all the defects in a zone, are inputted into the algorithm and used by the system during the area inspections. Each zone can have different sensitivities and defect sizes depending upon how important it is to have an area free of excess colorant, or other defects in the colorant.

Sensitivities for each zone of the image are set by an off-line test method. The method involves presenting multiple images with absences and excess colorant to multiple human observers. For example, when the observers decide to reject an image for a given excess, the sensitivity setting for excess is first set to an-insensitive level (e.g. 50) to ensure the lens passes when processed. The image is then reprocessed multiple times, each time with a slightly more sensitive setting (e.g. 49, 48, 47 , 46), until the image is rejected by the system. The sensitivity value that makes the image fail is used as a basis for the sensitivity setting for production. This method continues for multiple excesses and absences in each of the image zones until all sensitivities for each color being produced are determined as shown in Table A. Defect size thresholds and minimum defect sizes are also determined in a similar fashion and are included in Table A.

TABLE A

Parameters for a Number of Lens Molds

| Inspection Area | Sensitivity | Min. Defect Size mm² | Defect Size Threshold mm² |
|---|---|---|---|
| Enhancer Lens Mold-Blue | | | |
| Optical zone excess | 8 | 0.4 | 0.4 |
| Optical zone absence | 9 | 0.06 | 0.4 |
| Iris pattern zone excess | 15 | 0.4 | 0.4 |
| Iris pattern zone absence | 9 | 0.06 | 0.4 |
| Outer buffer zone excess | 16 | 0.5 | |
| Outer buffer zone absence | 18 | | |
| Knifeedge excess | 12 | 0.4 | |
| Enhancer Lens Mold-Green | | | |
| Optical zone excess | 7 | 0.4 | 0.4 |
| Optical zone absence | 7 | 0.06 | 0.4 |
| Iris pattern zone excess | 12 | 0.4 | 0.4 |
| Iris pattern zone absence | 9 | 0.06 | 0.4 |
| Outer buffer zone excess | 16 | 0.5 | 0.4 |
| Outer buffer zone absence | 18 | | |
| Knife edge zone excess | 12 | 0.4 | 0.4 |
| Opaque Lens Mold-Blue | | | |
| Optical zone excess | 8 | 0.06 | 0.06 |
| Iris pattern zone excess | 55 | 0.4 | 2 |
| Iris pattern zone absence | 30 | 0.4 | 2 |
| Outer buffer zone excess | 60 | | |
| Outer buffer zone absence | 60 | | 0.5 |
| Knife edge zone excess | 9 | 0.4 | 0.4 |
| Opaque Lens Mold-Green | | | |
| Optical zone excess | 7 | 0.06 | 0.06 |
| Iris pattern zone excess | 28 | 0.4 | 2 |
| Iris pattern zone absence | 26 | 0.4 | 2 |
| Outer buffer zone excess | 30 | | |
| Outer buffer zone absence | 30 | | 0.5 |
| Knife edge zone excess | 9 | 0.4 | 0.4 |

Therefore, the sensitivity of the optical zone is typically high and the allowable amount of excess colorant is very low. In contrast, the sensitivity of the iris pattern zone can be relatively lower to allow some excess colorant. Excess colorant is a cosmetic consideration in the Iris Pattern Zone and does not effect visual acuity, whereas excess colorant in the Optical Zone may affect visual acuity. Further, the knife edge zone, the area outside of the printed pattern, may also have lower sensitivity and a higher allowable area of excess ink than the optical zone for the same reason. All of these sensitivity values can be determined by the above described off-line method experimentation by analyzing acceptable and unacceptable tinted ophthalmic parts.

For enhancer lens molds the range of minimum defect size for excesses in the optical zone is about 0.8 mm to about 0.2 mm, preferably about 0.6 mm, to about 0.3 mm, most preferably, about 0.4 mm. For enhancer lens molds, the range of defect threshold size for excesses in the optical zone is about 0.8 mm² to about 0.2 mm², preferably about 0.6 mm² to about 0.3 mm², most preferably, about 0.4 mm². For enhancer lens molds the range of minimum defect size for absences in the optical zone is about 0.1 mm to about 0.01 mm, preferably about 0.08 mm, to about 0.04 mm, most preferably, about 0.06 mm. For enhancer lens molds, the range of defect threshold size for absences in the optical zone is about 0.8 mm² to about 0.2 mm², preferably about 0.6 mm² to about 0.3 mm², most preferably, about 0.4 mm².

For enhancer lens molds the range of minimum defect size for excesses in the iris pattern zone is about 0.8 mm to about 0.2 mm, preferably about 0.6 mm, to about 0.3 mm, most preferably, about 0.4 mm. For enhancer lens molds, the range of defect threshold size for excesses in the iris pattern zone is about 0.8 mm² to about 0.2 mm², preferably about 0.6 mm² to about 0.3 mm², most preferably, about 0.4 mm². For enhancer lens molds the range of minimum defect size for absences in the iris pattern zone is about 0.1 mm to about 0.01 mm, preferably about 0.08 mm, to about 0.04 mm, most preferably, about 0.06 mm. For enhancer lens molds, the range of defect threshold size for absences in the iris pattern zone is about 0.8 mm² to about 0.2 mm², preferably about 0.6 mm² to about 0.3 mm², most preferably, about 0.4 mm².

For enhancer lens molds the range of minimum defect size for excesses in the outer buffer zone is about 0.8 mm to about 0.2 mm, preferably about 0.6 mm, to about 0.3 mm, most preferably, about 0.4 mm. For enhancer lens molds, the range of defect threshold size for excesses in the outer buffer zone is about 0.8 mm² to about 0.2 mm², preferably about 0.6 mm² to about 0.3 mm², most preferably, about 0.4 mm².

For enhancer lens molds the range of minimum defect size for excesses in the knife edge zone is about 0.8 mm to about 0.2 mm, preferably about 0.6 mm, to about 0.3 mm, most preferably, about 0.4 mm. For enhancer lens molds, the range of defect threshold size for excesses in the knife edge zone is about 0.8 mm² to about 0.2 mm², preferably about 0.6 mm² to about 0.3 mm², most preferably, about 0.4 mm².

For opaque lens molds the range of minimum defect size for excesses in the optical zone is about 0.1 mm to about 0.01 mm, preferably about 0.08 mm, to about 0.03 mm, most preferably, about 0.06 mm. For opaque lens molds the range of defect threshold size for excesses in the optical zone is about 0.1 mm to about 0.01 mm, preferably about 0.08 mm, to about 0.03 mm, most preferably, about 0.06 mm.

For opaque lens molds the range of minimum defect size for excesses in the iris pattern zone is about 0.8 mm to about 0.2 mm, preferably about 0.6 mm, to about 0.3 mm, most preferably, about 0.4 mm. For opaque lens molds, the range of defect threshold size for excesses in the iris pattern zone is about 4.0 mm² to about 0.9 mm², preferably about 3.0 mm² to about 1.0 mm², most preferably, about 2.0 mm². For opaque lens molds the range of minimum defect size for absences in the iris pattern zone is about 0.8 mm² to about 0.2 mm, preferably about 0.6 mm to about 0.3 mm², most preferably, about 0.4 mm². For opaque lens molds, the range of defect threshold size for absences in the iris pattern zone is about 4.0 mm² to about 0.9 mm², preferably about 3.0 mm² to about 1.0 mm², most preferably, about 2.0 mm².

For opaque lens molds, the range of defect threshold size for excesses in the outer buffer zone is about 0.8 mm² to about 0.2 mm$^2$, preferably about 0.6 mm$^2$ to about 0.3 mm$^2$, most preferably, about 0.5 mm$^2$.

For opaque lens molds the range of minimum defect size for excesses in the knife edge zone is about 0.8 mm to about 0.2 mm, preferably about 0.6 mm, to about 0.3 mm, most preferably, about 0.4 mm. For enhancer lens molds, the range of defect threshold size for excesses in the knife edge zone is about 0.8 mm$^2$ to about 0.2 mm$^2$, preferably about 0.6 mm$^2$ to about 0.3 mm$^2$, most preferably, about 0.4 mm$^2$.

The algorithm analyzes the pixels in the image in the optical zone for changes in intensity from one pixel to another (i.e. contrast). Every pixel that is found above the intensity level corresponding to the sensitivity threshold is tracked in a database with its location, and the process continues with neighboring pixels to determine the size of the defect. The defect size is the area of neighboring pixels that are outside the allowed contrast range and the allowed patter area. (An area is determined based on the number of pixels, because the mold size is known and the total number of pixels within the area of the imaged mold is known.) Once the defect size has been determined, it is compared to the value for the minimum defect size area allowed. If the defect size is below the minimum allowed defect size the process of analyzing the intensity levels of pixels continues to find any other defects if any. For each zone all the defect sizes found are preferably summed and compared to the value for the defect size threshold. If this summation exceeds the defect size threshold, the image is rejected. To analyze the pixels, the eight neighboring pixels can be analyzed as describe in U.S. Pat. No. 5,500,732, earlier incorporated by reference. The eight neighboring pixel analysis continues for all the pixels within the zone, either until the defect areas or thresholds for the zone have been exceeded, or until the all the pixels in the zone have been analyzed. Each zone is analyzed in the same way; however the allowable range of sensitivities in the zone, the defect areas and the defect size thresholds can be adjusted for each zone.

The preferred method of printing the lens molds causes darker colorant intensities at the borders of the iris pattern zone; therefore, in the most preferred method of inspecting, the algorithm defines two additional areas called the inner buffer zone and the outer buffer zone. The inner buffer zone and the outer buffer zone sensitivities and defect sizes are set to different values from the rest of the iris pattern zone. The inner buffer zone is preferably 0.1 mm from the inside colorant border. The outer buffer zone is preferably 0.5 mm from the outside colorant border.

Alternatively, for colorant layers having sufficiently different and definable intensity ranges for each colorant layer in a single gray-scale image, e.g. for an ophthalmic part having a transparent enhancer layer and a dark opaque layer, the inspection could be performed by an algorithm that would determine based on the relative intensity values which intensity values correspond to which colorants. For example the lowest intensity value would correspond to no color, the next level of intensity values would correspond to the first colorant, e.g. transparent layer, and the next range of intensity values would correspond to the second colorant, e.g. the opaque layer. The values assigned to each colorant can also be checked by knowing the pattern for each colorant and comparing the pixel intensity values in the captured image to the expected location of the pixels in the patterns.

An alternate method of inspecting the zones would be to define, the numbers of pixels falling within specified ranges of intensities that correlate to the expected intensities of the colorants in the zone. As the intensities for pixels in a zone are read, they could be categorized into the specified ranges and each range summed. If the number of pixels within those defined ranges does not correspond to an expected number, based on the known patterns and colorants that make up the colorant layers, then the mold is rejected. Therefore, if a pattern of an acceptable intensity e.g. between 100-200 gray levels and if it covers 80% of the iris pattern zone, then the mold would pass. The accuracy of the inspection could be improved by more specifically defining intensity ranges at several different levels and the expected number of pixels within each range. As the pixels falling within the individual ranges and outside all the ranges are encountered they can be added to a record in the database that sums the pixels for the various ranges, and when the analysis is complete the individual totals for the individual ranges can be compared to the expected number for each of those ranges. If the pixels counted within each intensity range differ from the expected number of pixels and allowing for a small error margin that were mathematically calculated based on the expected pattern, then the mold is passed. If not the mold is rejected.

Alternatively, the pixels can be analyzed using the modified eight-neighbor method that skips every other pixel during its analysis to look for intensities within the zone. The modified eight-neighbor method is described in U.S. Pat. No. 5,500,732.

Alternately, index marks can be introduced into the pattern to allow for easy recognition of the rotational position and displacement of each colorant layer. Commercially available pattern recognition software could be adapted to locate the index mark and to measure the angle and displacement between each of the index marks. This technique would then provide a means to compare the relative position of the different colorant layers that does not rely on finding the center of an individual colorant layer. Note that these index marks would not be so obvious as to detract from the cosmetic appearance of the lens, but would be easily recognized by a pattern recognition system. The index marks can be lines or clusters of dots that differ from the rest of the pattern in the colorant layers, but that cannot be fully covered by the colorant pattern of another layer when properly applied. Alternatively the index marks could be added to the colorant layers in areas of those layers that are not expected to overlap. If the index mark or pattern could not be located on the ophthalmic part the part would be rejected.

Another optional step in the method of inspection includes determining the rotation of the colorant layers. Rotation of a colorant layer's pattern can be determined relative to the taught image. This is accomplished by comparing the angular position of one or more features in the pattern. The angle between a feature on the outer edge of the taught image and the corresponding feature on the captured image yields the amount of rotation. The algorithm can provide for multiple features or for the ability to repeat the search if an attempt to find a feature is unsuccessful, such as in the case of distortion of the applied colorant or a missing area of pattern on the captured image. The amount of rotation of the pattern is the angular difference between the expected or desired position of the feature in the taught image and the location of the feature in the captured image and can be averaged if multiple individual angle measurements are measured. For example if the tip of a "feather" in the feather layer is supposed to be located at the zero degree position, in line with the tab on the mold, and it is located in the pixel image at the one degree position instead, then the pattern was rotated by the pad printing process by one degree. In some embodiments of tinted lens designs, the rotation of a pattern may be very important if multiple colorant layers must be applied in exact angular positions to achieve a desired cosmetic effect.

The methods and associated apparatuses and systems, provide a multi-step process of analyzing the colorant on an ophthalmic part; however, the steps can be done individually or in any order depending upon the characteristics of the ophthalmic part to be inspected or the requirements of the manufacturer. If it is only important that concentricity of the patterns be checked, then that step can be done alone. If it is only important that the optical area be free of stray colorant and/or of a uniform intensity of colorant then that step can be done alone. However, if it is imperative that every pixel be analyzed to make sure that it matches the expected pattern, then that can be done also. Additionally the sensitivity of the system to the pixel intensity variations can be adjusted as desired, and can vary from high sensitivity, for example, within the optical zone to very low sensitivity, for example in the iris pattern zone.

Figure 6:
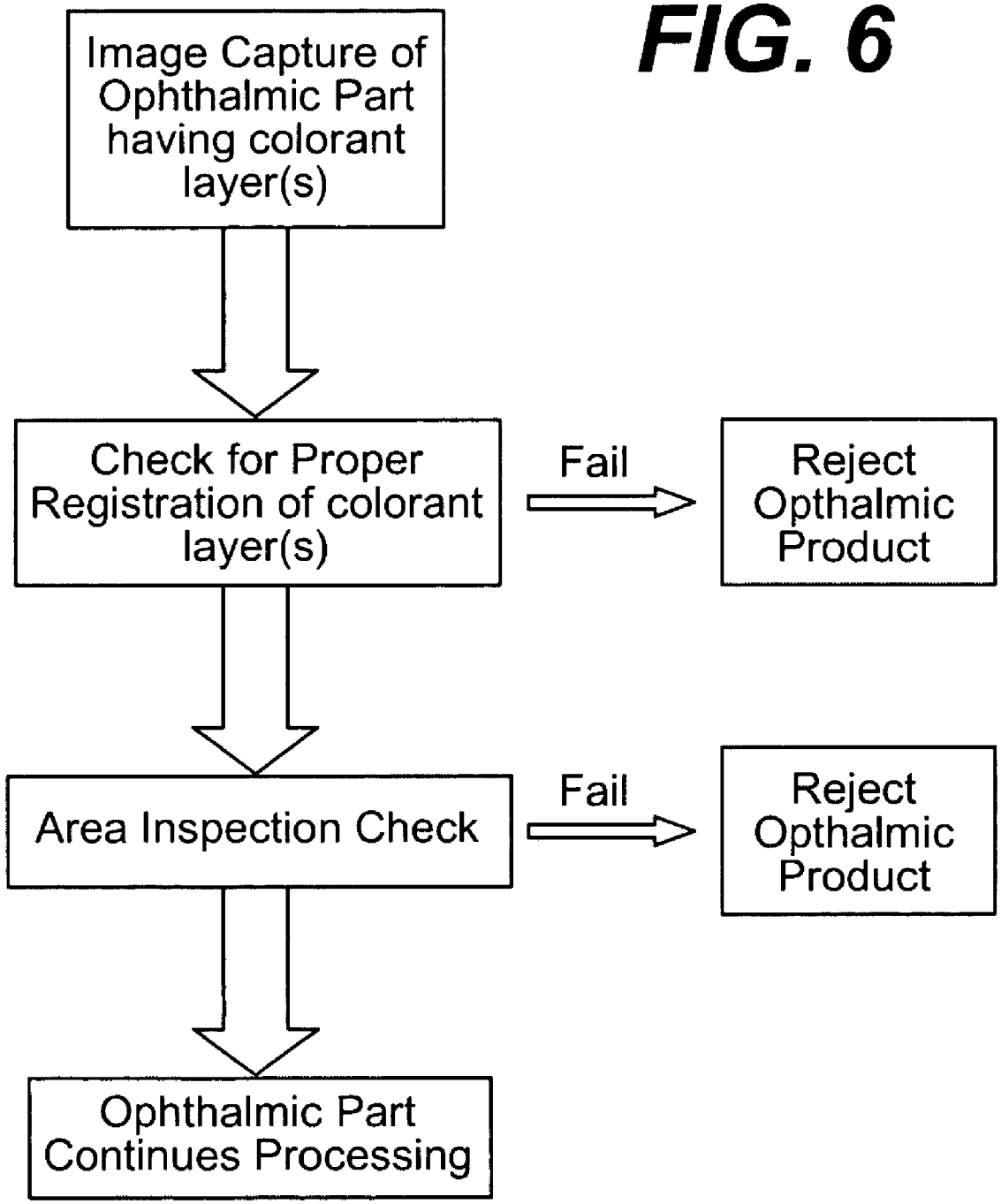
FIG. 6 is a flow chart the process steps of one embodiment of the invention.
Figure 7:
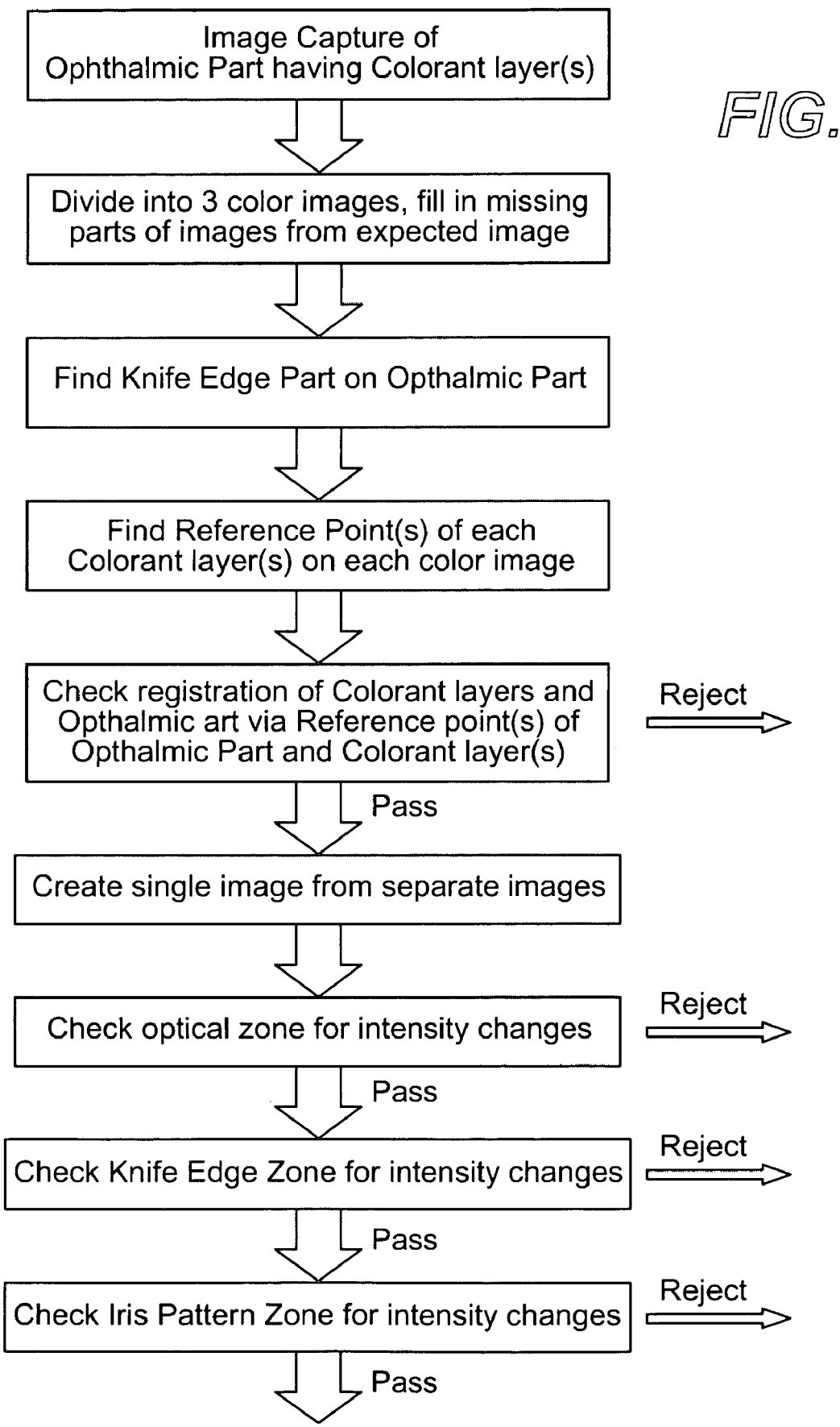
FIG. 7 is a in a flow chart the process steps of another embodiment of the invention.

FIGS. 6 and 7 both illustrate decision charts illustration specific embodiments of the invention. It is preferred that all of the steps of the invention are automated and occur on-line in a manufacturing line. Embodiments of the method invention are described in further detail in the following steps:

Method of Inspecting a Mold for an Opaque Lens
1. Capture the Image with a color or gray-level camera
2. Image is divided into RGB layers from the 3 chips of the color camera
3. Check for Proper Registration (centered locations) of the Image:
3.1 Find the knife-edge of the mold. This is the dark, narrow outer circle in the image of the plastic curve. It is not part of the print. Locate the center of the knife edge.
3.2 Scan left to right and up and down (grid pattern) to find the patterns in the opaque image.
3.3 Separate the full image (all 3 layers of color) into individual layers
3.4 Locate the center point of each individual layer
3.5 Locate the clock position of each pattern (i.e. rotation clockwise or counterclockwise when compared to the taught image for each layer).
3.6 Compare the position of the center point of the feather layer to the knife edge center. Likewise, compare the center point of the enhancer and striae layer to the center point of the knife edge. This is the concentricity measurement.
3.7 Compare the concentricity for the feather layer to the allowable concentricity.
3.8 If the concentricity is less than or equal to the allowable value, accept the image for this test and proceed with processing. If concentricity is above this value, reject the image. In addition, the relative center distance between the feather and the striae layer and between the feather and the foundation layer may be calculated. This may be compared to an allowable value and accepted or rejected accordingly.
4 Area. a Inspection Check:
4.1 Identify possible defect areas: For the optical zone, the central 4 mm of the image, identify pixels with excess color.
4.2 Calculate the Minimum Defect Size of possible defect areas. Through the calibration process, the size of each pixel is calculated using a known standard that is presented to the camera. Using the known number of mm per pixel, calculate the area of each possible defect area that was found in the step above.
4.3 Compare this area to the allowable Defect area=0.4 square mm. If the area of each possible defect is greater than or equal to the Minimum Defect Size, for the area is considered a defect.
4.4 Take the sum of all of the defect areas above and compare them to the Defect Size Threshold. If this sum is greater than or equal to this Threshold, the lens mold is rejected.
4.5 Calculation for each of the areas shown in FIG. 5 continues in the same way as described above for Optical Zone Excess. These calculations include:
4.6 Iris Pattern Zone—excess color and absence of color including special regions:
4.6.1.1 Inner Buffer zone—(an annulus of approximately 0.1 mm on the outer edge of the Iris pattern zone)—excess color and absence of color.
4.6.1.2 Outer Buffer zone—(an annulus of approximately 0.5 mm on the inner edge of the Iris pattern zone)—excess color and absence of color.
4.7 Knife Edge Zone—(the area between the outside of the pattern and the knife edge)—excess color.
5 The calculations are completed and compared to the allowable levels. Images with values that are not within the allowable levels are rejected. Processing may be discontinued after any of the calculations yield a rejection. Alternatively, al calculations can be completed to give an overall report to assist troubleshooting.

Figure 11:
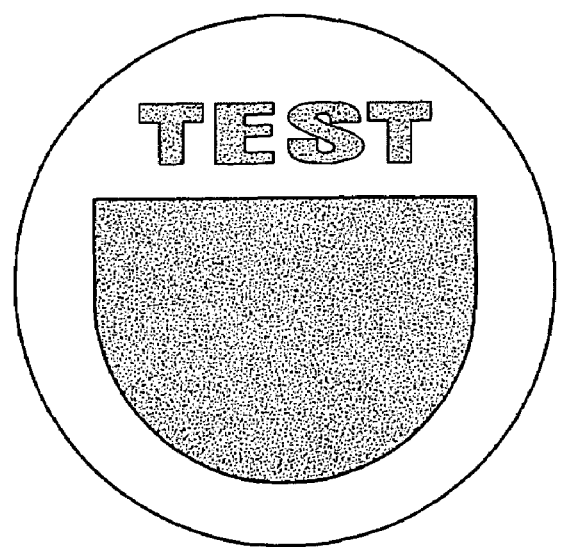
FIG. 11 illustrates the diagnostic print with the Test

Diagnostic Prints for Opaque Lens Molds
6.1 Similar processing can be done for the diagnostic opaque lens where the pattern is identical except for a "chop top" pattern for feather and striae layers instead of the standard round pattern. The diagnostic opaque pattern has the word "TEST" printed above the chop top pattern. Allowable missing and extra ink in the "TEST" word is selectable to allow for different print conditions and lettering completeness and legibility requirements. See FIG. 11. A good/bad report is sent to the Input/Output modules and then is communicated to the PLC computer for the material handling machine. The product is then accepted or rejected as per the good/bad report.

Figure 12:
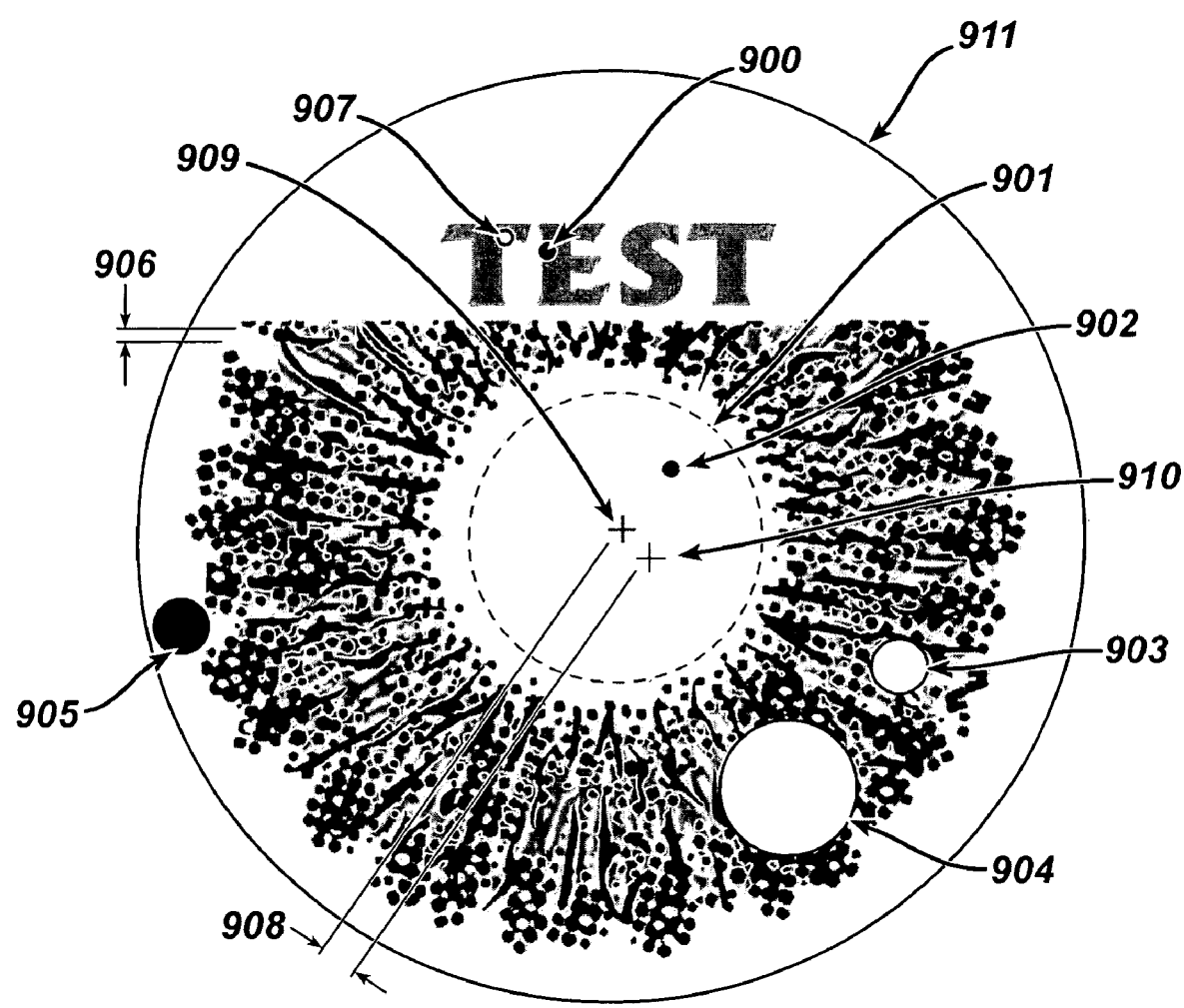
FIG. 12 illustrates an image of a diagnostic opaque lens mold

FIG. 12 illustrates an example of image of a diagnostic opaque lens mold. The area which defines the optical zone is represented by the dashed line 901. Excess colorant in the optical zone, 902 is shown and if the area of excess color is greater than 0.06 mm$^2$, the lens mold will be rejected. The center of the reference means, 909 is calculated from the knife edge of the image, 911. The colorant center is 910, and if the difference, 908, between the center of the reference means and the colorant center, 909 is greater is than 0.55 mm the lens mold will be rejected. Excess colorant near the diagnostic letters, 900, is shown and if the square area of such colorant is greater than 0.01 mm$^2$, the lens mold will be rejected. Any voids appear in the diagnostic letters, 907, if the area of the voids is greater than 0.035 mm$^2$, the lens mold will be rejected. If the overlap between the diagnostic lettering and the beginning of the chopped iris pattern is greater than 0.15 mm (906), the lens mold will be rejected. Excess colorant in the area outside of the iris pattern, 905, is shown and if that area if greater than 0.4 mm$^2$, the lens mold will be rejected. A void inside the iris pattern, 903 is shown. If this void has an area greater than 0.4 mm$^2$, the void is considered an attribute. If the sum of the area of all of the attributes in the iris pattern area, 904, is greater than 2.0 mm$^2$, the lens mold will be rejected.

Method Inspecting a Lens Mold for Enhancer Prints
1. Capture the Image with a color or gray-level camera
2. Image is divided into RGB layers from the 3 chips of the color camera
3. Check for Proper Registration (centered location) of the Image:
3.1 Find the knife-edge of the mold. This is the dark, narrow outer circle in the image of the plastic curve. It is not part of the print. Locate the center of the knife edge.
3.2 Scan left to right and up and down (grid pattern) to find the enhancer pattern.
3.3 Locate the center of the pattern.
3.4 Compare the position of the center of the enhancer layer to the knife edge center. This is the concentricity measurement.
3.5 Compare the knife edge center to the center of the enhancer layer. If the difference between the location of the two centers is less than or equal to the allowable value, accept the image for this test and proceed with processing. If this value is too high, reject the image.
4. Area Inspection Check:
4.1 Identify possible defect areas: For the optical zone, the central 4 mm of the image, identify pixels with excess color with the sensitivity set
4.2 Calculate the Minimum Defect Size of possible defect areas. Through the calibration process, the size of each pixel is calculated using a known standard that is presented to the camera. Using the known number of mm per pixel, calculate the area of each possible defect area that was found in the step above.
4.3 Compare this area to the allowable area (Optical Zone, Excess, Minimum Defect Size ). If the area of each possible defect is greater than or equal to the Minimum Defect Size, the area is considered a defect.
4.4 Take the sum of all of the defect areas above and compare them to the Defect Size Threshold . If this sum is greater than or equal to this Threshold, the lens is rejected.
4.5 Calculation for each of the areas continues in the same way as described above for Optical Zone Excess. Additional calculations include:
4.6 Optical Zone—absence of color
4.7 Iris Pattern Zone—excess color and absence of color including special regions:
4.8 Knife Edge Zone—(the area between the outside of the pattern and the knife edge)—excess color.
4.9 Non-uniformity—The non-uniformity of the enhancer layer is calculated to determine if the color is evenly distributed over an area. This is done in the Optical zone and Iris Pattern Zone with different sensitivity levels.
5. The calculations are completed and compared to the allowable levels. Images with values that are not within the allowable levels are rejected. Processing may be discontinued after any of the calculations yield a rejection. Alternatively, all calculations can be completed to give an overall report to assist troubleshooting.
6. Diagnostic Prints
6.1 Similar processing can be done for the diagnostic enhancer lens where the pattern is identical except for a "chop top" pattern is used instead of a standard round pattern. The diagnostic opaque pattern has the word "TEST" printed above the chop top pattern. Allowable missing and extra ink in the "TEST" word is selectable to allow for different print conditions and lettering completeness and legibility requirements.
7. A good/bad report is sent to the Input/Output modules and then is communicated to the PLC computer for the material handling machine. The product is then accepted or rejected as per the good/bad report.

Figure 13:
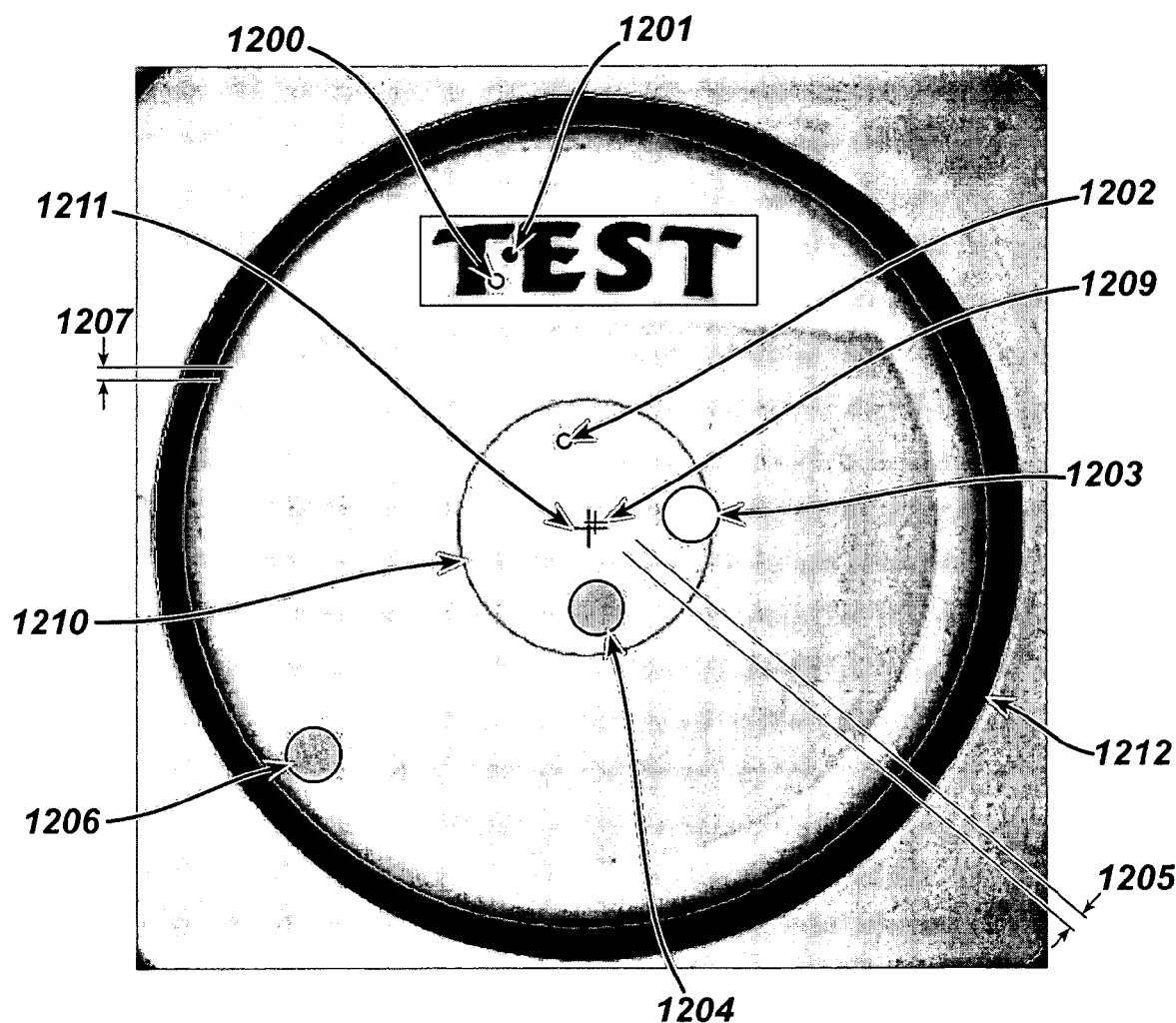
FIG. 13 is a scanned image of a diagnostic enhancer lens mold

FIG. 13 illustrates an image of an enhancer lens mold. The area that defines the optical zone is represented by the solid line 1210. Excess colorant in the optical zone, 1204 is shown and if the area of excess color is greater than 0.400 mm$^2$, the lens mold will be rejected. The center of the reference means, 1211 is calculated from the knife edge, 1212 of the image. The colorant center is 1209, and if the difference between the center of the reference means and the colorant center, 1205 is greater is than 0.3 mm the lens mold will be rejected. Excess colorant near the diagnostic letters, 1201, is shown and if the square area of such colorant is greater than 0.01 mm$^2$, the lens mold will be rejected. Any voids appear in the diagnostic letters, 1200, if the area of the voids is greater than 0.035 mm$^2$, the lens mold will be rejected. If the overlap, 1207, between the diagnostic lettering and the beginning of the chopped iris pattern is greater than 0.15 mm, the lens mold will be rejected. Excess colorant in the area outside of the iris pattern, 1206, is shown and if that area if greater than 0.4 mm$^2$, the lens mold will be rejected. A void inside the iris pattern, 1202 is shown. If this void has an area greater than 0.06 mm$^2$, the void is considered an attribute. If the sum of the area of all of the attributes in the iris patter area, 1203, is greater than 0.4 mm$^2$, the lens mold will be rejected.

We claim:
1. A method for inspecting ophthalmic parts comprising colorants the method comprising the steps of:
   a) capturing an image of said ophthalmic part comprising at least one colorant wherein said image comprises an array of pixels and said at least one colorant is present in a portion of said image;
   b) locating a reference means in said image of said ophthalmic part and finding the center of said reference means;
   c) locating at least one first pixel area in the portion of said image of said ophthalmic part comprising said at least one colorant;
   d) comparing the location of said at least one first pixel area to the location of a first pixel standard to determine the location of said colorant center; and
      comparing the location of the center of said reference means to the location of said colorant center to determine if said at least one colorant is properly located on said ophthalmic part.
2. The method of claim 1 wherein the reference means is the knife edge.
3. The method of claim 1 wherein the reference means is the outside edge.
4. The method of claim 1 wherein the first pixel area is located in the iris pattern and first pixel area comprises 10×10 pixels.
5. The method of claim 4 wherein the first pixel area comprises at least 5×5 pixels.
6. The method of claim 1 further comprising the step of
   e) comparing a second pixel standard to at least one second pixel area in the portion of said image of said ophthalmic part comprising a colorant to determine the location of the colorant center.
7. The method of claim 1 wherein all steps are automated and occur in an on-line manufacturing line.
8. The method of claim 7 further comprising the step of
   e) rejecting all ophthalmic parts wherein the difference between the location of the center of said reference and the location of the center of said colorant center are greater than about 0.550 mm.

9. The method of claim 1 further comprising the step of e) rejecting all ophthalmic parts wherein the difference between the location of the center of said reference and the location of the center of said colorant center are greater than about 0.550 mm.

10. A method for inspecting ophthalmic parts comprising colorants the method comprising the steps of:

a) capturing an image of said ophthalmic part comprising at least one colorant wherein said image comprises an array of pixels and said at least one colorant is present in a portion of said image;

b) locating a reference means in said image of said ophthalmic part and finding the center of said reference means;

c) analyzing said portion of said image comprising at least one colorant to determine the dimension of said portion and finding the colorant center of said image;

d) comparing the location of the center of said reference means to said colorant center to determine if said at least one colorant is properly located on said ophthalmic part.

11. The method of claim 10, further comprising the step of e) rejecting all ophthalmic parts wherein the difference between the location of the center of said reference and the location of the center of said colorant center are greater than about 0.550 mm.

12. The method of claim 10 wherein all steps are automated and occur in an on-line manufacturing line.

13. A method for inspecting ophthalmic parts comprising colorants the method comprising of the steps of:

a) capturing an image of said ophthalmic part having at least one colorant wherein said image comprises an array of pixels and said at least one colorant is present in a portion of said image;

b) capturing a reference image of a standard ophthalmic part wherein said reference image comprises an array of pixels and said at least one colorant is present in a portion of said reference image;

c) comparing the intensities of the image from step a) with the reference image from step b) to determine whether the image from step a) contains defects, d) rejecting all ophthalmic parts having excess colorant in the optical zone having an area of greater than about 0.06 mm$^2$, e) locating a reference means in said image of said ophthalmic part and finding the center of said reference means;

f) locating at least one first pixel area in the portion of said image of said ophthalmic part comprising said at least one colorant;

g) comparing the location of said at least one first pixel area to the location of a first pixel standard to determine the location of said colorant center; and h) comparing the location of the center of said reference means to the location of said colorant center to determine if said at least one colorant is properly located on said ophthalmic part.

14. The method of claim 13 further comprising the step of e) rejecting all ophthalmic parts having voids of colorant in the iris pattern, wherein said voids have a total area of great than about 2.0 mm$^2$.

15. The method of claim 13, wherein all of the steps are automated and occur in an on-line manufacturing line.

16. The method of claim 13, further comprising the step of i) rejecting all ophthalmic parts wherein the difference between the location of the center of said reference and the location of the center of said colorant center are greater than about 0.550 mm.

* * * * *